United States Patent [19]

Ascher

[11] 4,267,321

[45] May 12, 1981

[54] CEPHALOSPORIN DERIVATIVES

[75] Inventor: Gerd Ascher, Wörgl, Austria

[73] Assignee: Sandoz Ltd., Basel, Switzerland

[21] Appl. No.: 114,154

[22] Filed: Jan. 22, 1980

[30] Foreign Application Priority Data

Jan. 25, 1979 [AT] Austria .................................. 531/79

[51] Int. Cl.³ .......................................... C07D 501/20
[52] U.S. Cl. .................................... 544/030; 424/246
[58] Field of Search ..................... 544/30, 21; 424/246

[56] References Cited

U.S. PATENT DOCUMENTS

| 3,234,222 | 2/1966 | Fechtig et al. | 544/30 |
| 3,234,223 | 2/1966 | Fechtig et al. | 544/30 |
| 3,853,863 | 12/1974 | Jackson et al. | 544/30 |
| 3,880,846 | 4/1975 | Breuer et al. | 424/246 |

*Primary Examiner*—Nicholas S. Rizzo
*Attorney, Agent, or Firm*—Gerald D. Sharkin; Robert S. Honor; Timothy G. Rothwell

[57] ABSTRACT

Novel Cephalosporin C derivatives, their production and their use in isolating Cephalosporin C from culture filtrates for subsequent conversion to 7-aminocephalosporanic acid.

7 Claims, No Drawings

CEPHALOSPORIN DERIVATIVES

This invention provides compounds of formula I,

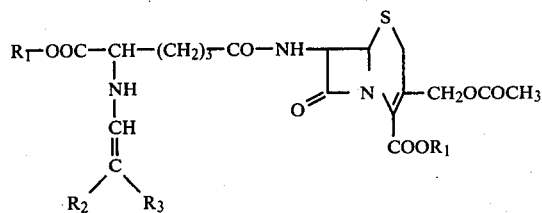

in which the radicals $R_1$, which may be the same or different, each signifies hydrogen or the residue of an ester grouping,
and $R_2$ and $R_3$, which may be the same or different, each signifies hydrogen, nitro, cyano or lower alkoxycarboxyl.

The invention also provides a process for the production of compounds of formula I, characterised by
(a) reacting a compound of formula II,

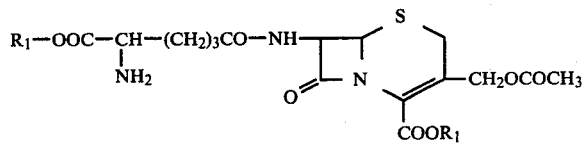

in which $R_1$ is as defined above, with a compound of formula III,

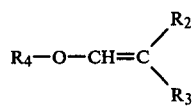

in which $R_2$ and $R_3$ are as defined above, and $R_4$ is lower alkyl,
(b) producing a compound of formula Ia,

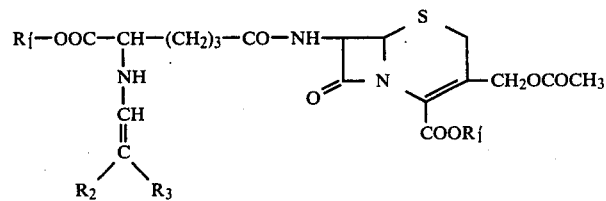

in which $R_2$ and $R_3$ are as defined above, and one of the radicals $R_1'$ is the residue of an ester grouping and the other is hydrogen or the residue of an ester grouping,
by esterifying a compound of formula Ib,

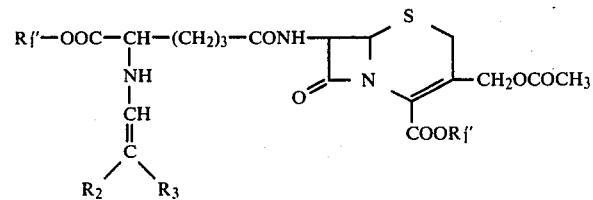

in which $R_2$ and $R_3$ are as defined above, and the radicals $R_1''$ are each hydrogen or the residue of an ester grouping, at least one however being hydrogen.

The process (a) may suitably be effected in an inert solvent or solvent mixture, for example in an aqueous medium or a mixture of water and a water-miscible solvent, e.g. ethanol or acetone, preferably however in water. The reaction is suitably effected at a temperature of from room temperature to 60° C., preferably from 30° to 40° C., in particular at about 35° C. The compounds of formula II in which $R_1$ is hydrogen may be employed in the form of salts, e.g alkali metal salts, for example the mono- or disodium salt. Such compounds may also be in the form of hydrates.

Process (b) may be carried out in known manner for the production of corresponding esters of Cephalosporin C (the compound of formula II in which each $R_1$ is hydrogen), as for example illustrated in the examples hereinafter. The esterification is suitably effected in an inert solvent, such as dichloromethane, using appropriate reactive derivatives of the ester residue to be introduced. For example benzhydryl esters may be produced by reaction with benzophenonehydrazone, e.g. in the presence of manganese dioxide, while trialkylsilyl esters may be produced by reaction with trialkylhalosilanes, e.g. in the presence of a base such as pyridine, triethylamine, or N,N-dimethylaniline, or mixtures thereof.

The resulting compounds of formula I may be isolated and purified using conventional techniques. Where required the compounds in which one or both $R_1$'s are hydrogen, may be converted into salt forms, e.g. alkali metal salt forms, in conventional manner, and vice versa.

The compounds of formula I are useful as intermediates. In particular, they may be converted, by well-known deacylation procedures, into 7-ACA and esters thereof, of formula IV,

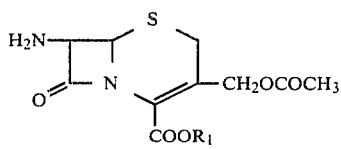

in which $R_1$ is as defined above.

The compounds of formula IV are of course key intermediates for the production of semi-synthetic cephalosporins.

The deacylation of the compounds of formula I, to form the compounds of formula IV, may be accomplished in manner well-known for the deacylation of for example Cephalosporin C to produce 7-ACA. A preferred process is the so-called iminohalide/iminoether deacylation route, involving formation of the e.g. iminochloride, by reaction with e.g. $PCl_5$, conversion to the iminoether by treatment with e.g. a lower ethanol, and hydrolysis, e.g. in aqueous acid. This process was first described for deacylating Cephalosporin C, in U.K. Pat. No. 1,041,985, and equivalents but there have been numerous further publications on modifications of this process (e.g. U.K. Pat. Nos. 1,119,806; 1,239,814; 1,241,655; 1,270,448).

Compounds of formula IV in which $R_1$ is the residue of an ester grouping may either be used as such in further reactions, or may be converted to 7-ACA itself ($R_1$=H) in known manner, e.g. by hydrolysis, which may occur spontaneously in the reaction mixture in the case of some esters.

As is well-known, the obtention and isolation of strongly hydrophilic antibiotics, such as Cephalosporin C, presents difficulties. The antibiotic must either be purified by a series of laborious adsorption- or chromatographic steps, or must be converted by chemical derivatisation of the free amino group of the side chain, into a derivative which is extractable under acid pH conditions.

The chemical derivatisation is normally accomplished by acylation with acid chlorides, which must, because of aqueous surroundings which are present, normally be used in great excess. Side reactions can therefore occur and the antibiotic must be isolated and purified laboriously.

The formation of the compounds of the invention can, it has been found, be accomplished readily and in good yields in Cephalosporin C culture filtrates. Of particular advantage is that the olefines of formula III are, to a large extent, stable against aqueous hydrolysis, so that great excesses do not, unlike the known processes, have to be employed. Side reactions are, to a large extent, avoided.

The present invention thereby provides a ready means for isolating Cephalosporin C in good yields in the form of a derivative of formula I, for subsequent conversion in known manner and in good yields, to 7-ACA or an ester thereof.

In the compounds of formula I, the ester grouping formed by $R_1$ may be any conventional ester protecting group employed in cephalosporin chemistry, in particular in deacylation processes for the obtention of 7-ACA. Preferred ester groupings are, however, the trialkylsilyl and benzhydryl groups. The groups $R_1$ and the groups $R_2$ and $R_3$, when these are both other than hydrogen, are preferably the same. As used herein with reference to alkoxy or alkyl radicals, the term "lower" means preferably of 1 to 4, e.g. 1 to 2 carbon atoms.

The starting materials of formulae II and III are either known or may be produced in conventional manner from available materials.

The following Examples illustrate the invention. All temperatures are in ° C.

EXAMPLE 1

N-(2-nitro-2-carbethoxy)-vinyl-(1)-cephalosporin C 14.2 g of cephalosporin C monosodium salt dihydrate are dissolved in 30 ml of water. 2.52 g of sodium bicarbonate are added in small portions with stirring. After the gas evolution has been completed, the residual carbon dioxide is removed from the solution by warming to approximately 35°. 10 ml of water are added, followed by 5.7 g of (ethoxymethylene) (nitro)acetic acid ethyl ester, dissolved in 15 ml of acetone. After stirring for an hour at room temperature, the acetone is evaporated off and the aqueous phase is extracted with ethyl acetate. The pH of the aqueous phase is adjusted to 2 and the mixture is extracted with fresh ethyl acetate. The ethyl acetate phase is washed with water and dried. After removal of the solvent, the residue is rubbed with diisopropyl ether and dried, to obtain the heading compound, m.p. 95°–100° (decomp.).

EXAMPLE 2

N-(2-nitro-2-carbethoxy)-vinyl-(1)-cephalosporin C

The heading compound is obtained in manner analogous to Example 1, except that 14.2 g of cephalosporin C monosodium salt dihydrate are dissolved in 300 ml of water and this solution is adjusted to pH 8 with 1 N NaOH. The (ethoxymethylene) (nitro) acetic acid ethyl ester is dissolved in 150 ml of acetone.

EXAMPLE 3

N-(2-nitro-2-carbethoxy)-vinyl-(1)-cephalosporin C 1,000 ml of the purified culture filtrate of a cephalosporin C fermentation, from which the antibiotically inactive impurities have been removed in conventional manner, containing 12 g of active agent per liter is concentrated by azeotropic distillation with butanol under vacuum to about 300 ml. The aqueous solution is filtered over Filtercel and the filtrate is adjusted to 8 pH with 1 N NaOH. To this solution, 5.7 g of (ethoxymethylene) (nitro) acetic acid ethyl ester, dissolved in 150 ml of acetone, are added. After 2 hours stirring at room temperature, the heading compound is worked up, as described in Example 1.

EXAMPLE 4

N-(2,2-dicarbethoxy)-vinyl-(1)-cephalosporin C 14.2 g of cephalosporin C monosodium salt dihydrate are dissolved in 30 ml of water and the solution of the disodium salt is prepared as in Example 1. To this solution, 6 ml of ethoxymethylenemalonic acid diethyl ester in 15 ml of acetone are added and the mixture is stirred at room temperature for 6 hours. The heading compound is worked up as in Example 1 and is rubbed with diisopropyl ether and dried in vacuo over phosphorous pentoxide, m.p. >80° (decomp.).

EXAMPLE 5

N-(2,2-dicarbethoxy)-vinyl-(1)-cephalosporin C 14.2 g of cephalosporin C disodium salt are dissolved in 150 ml of water and the pH is adjusted to 8.2 with 1 N NaOH. To this solution, 6 g of (ethoxymethylene) malonic acid diethyl ester, in 50 ml of acetone, are added and the mixture is stirred at 30° for 5 hours. The heading compound is worked up as in Example 1.

EXAMPLE 6

N-(2,2-dicarbethoxy)-vinyl-(1)-cephalosporin C

The heading compound is obtained in the same manner as in Example 3, except that the culture filtrate is first concentrated to 150 ml and that a solution of 6 ml of (ethoxymethylene) malonic acid diethyl ester in 150 ml of acetone is added and the mixture is stirred for 8 hours at 35°.

EXAMPLE 7

N-(2-carbethoxy-2-cyano)-vinyl-(1)-cephalosporin C 14.2 g of cephalosporin C monosodium salt dihydrate are dissolved in 30 ml of water and the equivalent amount of 1 N NaOH is added. To this solution, 4.84 g of (ethoxymethylene) (cyano) acetic acid ethyl ester, in 15 ml of acetone are added, and the mixture is stirred at romm temperature for 4 hours. The alkaline solution is extracted with ethyl acetate and the organic phase is discarded. The aqueous phase is acidified to pH 2 and extracted with ethyl acetate. The ethyl acetate extract is washed with water and dried. Removal of the solvent and rubbing with diisopropyl ethyl ether, yields the heading compound, m.p. 100°–113° (decomp.).

EXAMPLE 8

N-(2,2-dicyano)-vinyl-(1)-cephalosporin C

The heading compound is obtained in the same manner as in Example 1, employing a solution of 3.66 g of ethoxymethylene malonic acid dinitrile, dissolved in 15 ml of acetone, m.p. 98°–110° (decomp.).

EXAMPLE 9

N-(2-nitro-2-carbethoxy)-vinyl-(1)-cephalosporin C bis-benzhydryl ester 8.62 g of benzophenonehydrazone are dissolved in 86 ml of dichloromethane and stirred with 13 g of manganese dioxide for an hour. The manganese dioxide is filtered off and a solution of 11.16 g of N-(2-nitro-2-carbethoxy)-vinyl-(1)-cephalosporin C is added. The mixture is stirred at room temperature until gas evolution ceases. The solvent is evaporated off and the residue is taken up in ethyl acetate. The ethyl acetate phase is extracted first with sodium bicarbonate solution and then with water and then dried with sodium sulphate. After removal of the solvent, the heading compound remains as a honey-coloured residue, which is crystallised by rubbing with diisopropyl ether, m.p. 80°–83°.

EXAMPLE 10

N-(2,2-dicarbethoxy)-vinyl-(1)-cephalosporin C bis-benzhydryl ester

The heading compound is produced as in Example 9 from 11.72 g of N-(2,2-dicarbethoxy)-vinyl-(1)-cephalosporin C and 8.62 g of benzophenonehydrazone, m.p. 65°–68°.

EXAMPLE 11

7-Aminocephalosporanic acid (7-ACA)

2.85 g of N-(2-nitro-2-carbethoxy)-vinyl-(1)-cephalosporin C, are suspended in 150 ml of dry dichloromethane and 3.02 ml of pyridine are added, whereupon a solution forms. 5.02 ml of trimethylchlorosilane are added and the mixture is stirred for 2 hours at +30°. The mixture is cooled to −12° and a further 6.34 ml of pyridine are added. A solution of 4.15 g of phosphorous pentachloride in 50 ml of dry dichloromethane is added in a manner such that the temperature does not rise above −10°. The mixture is stirred for a further 40 minutes at −10°. To the solution is added, dropwise, 78 ml of methanol, pre-cooled to −20°, so that the temperature does not rise above −10°. The mixture is stirred for 30 minutes at −10° and 3 minutes at room temperature. The mixture is evaporated on a rotary evaporator and the residue is taken up in 10 ml of 50% formic acid, whose pH has been adjusted to 2 by addition of triethylamine. The mixture is stirred for a further 45 minutes at room temperature and then adjusted to pH 3.3 by addition of triethylamine. The mixture is seeded with a little 7-ACA and the title compound crystallises on standing in the refrigerator overnight, is filtered off, washed with dichloromethane and ether and dried.

EXAMPLE 12

7-Aminocephalosporanic acid (7-ACA)

In the same manner as in Example 11, the heading compound is obtained from 2.93 g of N-(2,2-dicarbethoxy)-vinyl-(1)-cephalosporin C.

EXAMPLE 13

7-Aminocephalosporanic acid benzhydryl ester 4.46 g of N-(2-nitro-2-carbethoxy)-vinyl-(1)-cephalosporin C bis-benzhydryl ester are dissolved in 35 ml of dry dichloromethane and 4.03 ml of pyridine are added. The solution is cooled to −20° and a solution of 2.4 g of phosphorous pentachloride in 50 ml of dry dichloromethane is added, dropwise, with stirring so that the temperature does not rise above −10°. The mixture is stirred for 45 minutes at −10°. 28 ml of methanol, pre-cooled to −10°, are added in 1 portion so that the temperature rises to 0°. The mixture is stirred for a further 30 minutes at −10° and 1 hour at room temperature. 100 ml of ice-cooled 1 N hydrochloric acid are added and the mixture is stirred for a further 45 minutes at 0°. The pH is adjusted to 8 by addition of 2 N NaOH and the aqueous phase is separated. The organic phase is dried and evaporated. The heading compound results upon rubbing with diisopropyl ether.

EXAMPLE 14

7-Aminocephalosporanic acid benzhydryl ester

The heading compound is obtained in the same manner as in Example 13 from 4.59 g of N-(2,2-dicarbethoxy)-vinyl-(1)-cephalosporin C bis-benzhydryl ester.

EXAMPLE 15

7-Aminocephalosporanic acid (7-ACA)

2.79 g of N-(2-nitro-2carbethoxy)-vinyl-(1)-cephalosporin C are suspended in 30 ml of dry methylene chloride and the solution is formed by addition of 0.7 ml of triethylmamine. To this solution, 1.5 ml of N,N-dimethylaniline and 1.27 ml of trimethylchlorosilane are added and the mixture is stirred for a further hour at room temperature. The mixture is cooled to −15° and 1.25 g of phosphorous pentachloride are added in portions. The mixture is stirred for a further 2 hours at −15° and 15 ml of butanol are added dropwise so that the temperature does not exceed −10°. After 2 hours stirring at −10°, 30 ml of water are added, the phases are separated and the aqueous phase is adjusted to pH 3.5 and covered with a layer of 10 ml of methylisobutyl ketone. The resulting precipitate is cooled overnight, filtered off and washed with propanol.

EXAMPLE 16

7-Aminocephalosporanic acid (7-ACA)

1.61 g of phosphorous pentachloride are suspended in 20 ml of dried dichloromethane and mixed, with stirring, with 0.63 ml of pyridine. The mixture is stirred for half an hour at 30° and cooled to 0°. 4.46 g of N-(2-nitro-2-carbethoxy)-vinyl-(1)-cephalosporin C bis-benzhydryl ester in a number of portions are added and the mixture is stirred for a half an hour at 5°. The mixture is cooled to −15° and mixed, with stirring, with 9 ml of butanol. The mixture is stirred for a further 30 minutes at −10° and 30 minutes at room temperature and mixed with 10 ml of ice-water. The dichloromethane phase is washed with water and evaporated to dryness. The residue is taken up in 4 ml of formic acid and stirred for 1 hour at 50°. The formic acid is removed in vacuo and the residue is distributed between 25 ml of 0.2 N HCl and ethyl acetate. The aqueous phase is adjusted to pH 3.5 to crystallise the heading compound.

What is claimed is:

1. 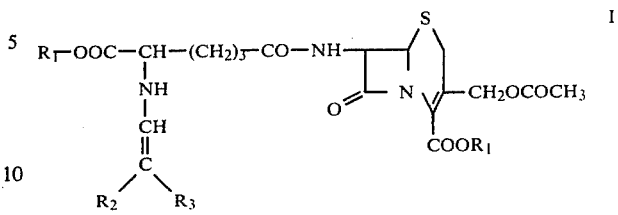

in which each $R_1$ independently represents hydrogen or an ester protecting group,
and $R_2$ and $R_3$, each independently represent hydrogen, nitro, cyano or lower alkoxy carbonyl, or and alkali metal salt provided at least one $R_1$ represents hydrogen.

2. The compound of claim 1 which is N-(2-nitro-2-carbethoxy)-vinyl-(1)-cephalosporin C.

3. The compound of claim 1 which is N-(2,2-dicarbethoxy)-vinyl-(1)-cephalosporin C.

4. The compound of claim 1 which is N-(2-carbethoxy-2-cyano)-vinyl-(1)-cephalosporin C.

5. The compound of claim 1 which is N-(2,2-dicyano)-vinyl-(1)-cephalosporin C.

6. The compound of claim 1 which is N-(2-nitro-2-carbethoxy)-vinyl-(1)-cephalosporin C bis-benzhydryl ester.

7. The compound of claim 1 which is N-(2,2-dicarbethoxy)-vinyl-(1)-cephalosporin C bis-benzhydryl ester.

* * * * *

UNITED STATES PATENT AND TRADEMARK OFFICE
CERTIFICATE OF CORRECTION

PATENT NO. : 4,267,321

DATED : May 12, 1981

INVENTOR(S) : Gerd Ascher

It is certified that error appears in the above-identified patent and that said Letters Patent is hereby corrected as shown below:

Column 8, Claim 1; directly above the structural formula, please insert -- Compounds of formula I, -- .

Signed and Sealed this

Eighth Day of February 1983

[SEAL]

Attest:

GERALD J. MOSSINGHOFF

Attesting Officer

Commissioner of Patents and Trademarks